United States Patent [19]

Wunder et al.

[11] 4,296,266

[45] Oct. 20, 1981

[54] PROCESS FOR THE MANUFACTURE OF LOWER OLEFINS FROM METHANOL/WATER MIXTURES

[75] Inventors: Friedrich Wunder, Flörsheim am Main; Ernst I. Leupold, Neu-Anspach; Horst Hachenberg, Walluf; Hans-Joachim Schmidt, Königstein, all of Fed. Rep. of Germany

[73] Assignee: Hoechst Aktiengesellschaft, Frankfurt am Main, Fed. Rep. of Germany

[21] Appl. No.: 169,629

[22] Filed: Jul. 16, 1980

[30] Foreign Application Priority Data

Jul. 18, 1979 [DE] Fed. Rep. of Germany ....... 2928922

[51] Int. Cl.$^3$ ............................ C07C 1/00; C07C 1/24
[52] U.S. Cl. .................... 585/640; 252/455 Z
[58] Field of Search ............................ 585/640, 639; 252/455 Z

[56] References Cited

U.S. PATENT DOCUMENTS

| | | | |
|---|---|---|---|
| 3,321,521 | 5/1967 | Kerr | 252/455 Z X |
| 4,156,698 | 5/1979 | Dwyer et al. | 585/640 X |
| 4,247,731 | 1/1981 | Wunder et al. | 585/640 |

FOREIGN PATENT DOCUMENTS 6501 9/1980 European Pat. Off. ............ 585/640

*Primary Examiner*—John Doll
*Attorney, Agent, or Firm*—Curtis, Morris & Safford

[57] ABSTRACT

Olefins having from 2 to 4 carbon atoms are manufactured from methanol and/or dimethyl ether in the presence of water and a manganese-containing aluminum silicate catalyst. Before or after application of the manganese, the aluminum silicate is washed with a solution of ethylene-diaminetetraacetic acid or tartaric acid adjusted to a pH of from 3 to 7 by means of a base.

6 Claims, No Drawings

PROCESS FOR THE MANUFACTURE OF LOWER OLEFINS FROM METHANOL/WATER MIXTURES

German Offenlegungsschrift No. 2,755,229 describes a process for the manufacture of lower olefins from methanol and/or dimethyl ether, in which the conversion of methanol takes place on aluminum silicate catalysts containing manganese. These catalysts must periodically be regenerated, that is to say freed from by-products which have been formed, and this can already be effected at relatively low temperatures of 300° to 500° C., most advantageously at the reaction temperature itself, using air or other gases containing oxygen. If methanol which contains no water or only a little water is employed, these catalysts can be regenerated very frequently without a reduction in their efficiency or selectivity occurring. However, in the reaction described, a water/methanol mixture is obtained if the conversion is not complete. The methanol present in this mixture must be recovered. However, unless expenditure is considerable, only a methanol which contains water to a greater or lesser extent is obtained on distillation. The presence of water indeed has a favorable effect on the selectivity with regard to ethylene—in particular the proportion of butene is decreased—but it has been found that some manganese aluminosilicate catalysts lose a significant proportion of their activity under the reaction conditions and can be regenerated again only a few times. Careful dehydration of the methanol before recycling indeed solves this problem, but means a high expenditure of energy.

There thus arose the object of developing a catalyst which is stable towards relatively large amounts of water under the reaction conditions.

A process has now been found for the preparation of $C_2$–$C_4$-olefins from methanol and/or dimethyl ether in the presence of water, on an aluminum silicate catalyst containing manganese, which comprises washing the catalyst with a solution of ethylenediaminetetraacetic acid or tartaric acid with a pH of 3 to 7. A pH of 4 to 5 is preferred. The washing is preferably undertaken before application of the manganese. Washing with ethylenediaminetetraacetic acid solution is particularly suitable.

Examples of possible aluminum silicates are the customary, amorphous acid cracking catalysts, which in general contain about 13 to 25% by weight of aluminum oxide and 75 to 87% by weight of silica. Furthermore, naturally occurring or synthetic crystalline aluminum silicates are also suitable, such as those which are known, for example, by names such as faujasites, zeolites, chabasites, analcime, gismondite, gmelinite, natrolite, mordenites and erionites, or generally as molecular sieves.

In the case of crystalline molecular sieves with various pore diameters, it is appropriate to use those with large pores, for example pores of 5 A and more.

To manufacture the catalyst according to the invention, the aluminum silicates are washed, before or after application of the manganese, with a solution of ethylenediaminetetraacetic acid or tartaric acid which has been adjusted to pH 3–7, preferably to pH 4–5, with a base. Examples of suitable bases are lithium hydroxide, sodium hydroxide, potassium hydroxide, rubidium hydroxide and caesium hydroxide, especially sodium hydroxide and potassium hydroxide. Alkali metal salts of weak acids, such as carbonates, are also suitable.

The concentration of the solutions of ethylenediaminetetraacetic acid or tartaric acid can be varied within wide limits, from about a 1% strength solution to a saturated solution; solutions which are about saturated at room temperature are preferred. The temperature of these solutions is preferably between 0° C. and 50° C. Preferred solvents are water, methanol, formamide, dimethylformamide or mixtures thereof, and in particular water. After the washing with ethylenediaminetetraacetic acid solution or tartaric acid solution, the catalyst is washed with pure solvent to remove the ethylenediaminetetraacetic acid or tartaric acid. Activation of the catalyst according to the invention is preferably effected by subsequent application (but prior application may also be appropriate) of 0.1 to 10% by weight of manganese, in the form of manganese salt solutions, to the aluminum silicate. For this, for example, the aluminum silicate can be impregnated with a solution of manganese salts and then dried. Preferred solvents for the manganese salts are water, methanol, formamide, dimethylformamide or also a mixture thereof, and in particular water. The manganese can also be applied by prolonged action of a manganese salt solution on the aluminum silicate and subsequent rinsing with pure solvent and drying.

If molecular sieves are used, one of the customary methods for impregnating these materials with a metal cation can be chosen; this method can be replacement of the cations originally present on the molecular sieve by manganese, and it can also be preliminary conversion of the molecular sieve into the proton form with subsequent treatment with a solution of a manganese salt.

Furthermore, it has frequently proved to be advantageous for a high selectivity also to use other elements as co-catalysts, in addition to the manganese. Elements which are suitable are those which occur in the monovalent, divalent or trivalent state in their compounds, such as, for example, the alkali metals (in particular lithium, sodium and potassium), the alkaline earth metals (in particular magnesium and calcium), zinc, lanthanum, rare earths (such as praseodymium, neodymium, samarium, gadolinium or also their mixtures, such as in didymium) and beryllium.

The further metal salts having a co-catalytic action can be applied simultaneously with the manganese salt, for example by mixing a solution of the manganese salt with a solution of one or more of the other metal salts and allowing this mixture to act on the aluminum-silicate.

However, they can also be applied successively to the aluminum silicate.

Possible manganese salts are all the soluble salts, for example the chloride, sulfate, nitrate, formate, acetate, propionate, butyrate, lactate, citrate and tartrate, and salts of malic acid. The corresponding statement applies to the co-catalysts. If common solutions of manganese and the element having a co-catalytic action are used, the reciprocal effect on the solubility should be taken into consideration, that is to say if calcium or barium is employed, it is inappropriate to use sulfate as the anion.

After the impregnation, the catalysts are dried under normal pressure, in vacuo or under increased pressure, at normal temperature or at elevated temperatures. In general, the drying temperatures are below 600° C., and are preferably between 100° and 200° C.

If methanol is used as the starting material, it is possible either to pass methanol directly over the catalyst according to the invention or first to convert it into dimethyl ether in a preliminary dehydration reaction on a customary dehydration catalyst such as aluminum oxide or aluminum silicate and then to pass the dimethyl ether over the catalyst according to the invention.

However, it is also possible to use mixtures of methanol and dimethyl ether or dimethyl ether by itself as the starting substance.

The starting components methanol and/or dimethyl ether can also be diluted with inert gases and employed in the reaction. Nitrogen, carbon dioxide and alkenes, for example, are suitable for lowering the partial pressure. For this purpose, however, the reaction can also be carried out under a reduced pressure of down to 0.1 bar.

The water content of the starting materials can be varied within wide limits, from anhydrous up to about 80% of water, but higher amounts of water give rise to higher evaporation and distillation costs.

The reaction temperature is in general between 300° and 500° C., preferably between 350° and 450° C. and particularly preferably between 380° and 420° C. If the reaction conditions are chosen such that only an incomplete conversion of methanol and/or dimethyl ether is achieved, the unconverted portions can be separated off and recycled.

The alkenes manufactured by the process according to the invention can be separated from the alkanes formed as a by-product and from one another by customary methods, for example by distillation.

A process which permits the manufacture of industrially important lower alkenes from methanol and/or dimethyl ether in the presence of water in a particularly selective and hence economic manner is thus available. The catalyst according to the invention can be manufactured in a surprisingly simple manner from readily accessible substances.

The following examples illustrate the process according to the invention:

COMPARISON EXAMPLE 1

300 ml of a commercially available chabasite/erionite mixture in the form of extruded particles are covered with a layer of 300 ml of saturated, aqueous manganese acetate solution, and after 48 hours are washed with water and dried. 202 g of catalyst containing 3.6% of Mn are obtained. 89.1 g of methanol per hour are passed over this catalyst at 400° C. 25.8 l of a gas consisting of 31.0% by weight of ethylene, 32.5% by weight of propylene, 5.4% by weight of butenes, 6.8% by weight of methane, 1.4% by weight of ethane, 19.3% by weight of propane, 3.4% by weight of butane and 0.3% by weight of other compounds, and 4.5 g of dimethyl ether, 9.2 g of methanol and 43.3 g of water are obtained per hour. This corresponds to a conversion of methanol of 89.6%, a selectivity for $C_2$–$C_4$-olefins of 68.8% and a selectivity for $C_2$–$C_4$-hydrocarbons of 93%, if the dimethyl ether formed and the unreacted methanol are recycled.

When its efficiency decreases, the catalyst is regenerated by passing air over at 430° C., whereupon the efficiency of the fresh catalyst is achieved. Even after 26 regeneration cycles, no exhaustion of the catalyst is observed.

COMPARISON EXAMPLE 2

Comparison Example 1 is repeated, with the only difference that 45.4 g/h of water are added to the feed methanol. When 92.3 g of methanol and 45.4 g of water are fed in per hour, 26.2 l per hour of a gas containing 34.2% by weight of ethylene, 33.7% by weight of propylene, 6.3% by weight of butenes, 7.2% by weight of methane, 1.3% by weight of ethane, 14.7% by weight of propane, 2.4% by weight of butane and 0.2% by weight of other compounds, and 4.3 g of dimethyl ether, 8.9 g of methanol and 44.2 g of water per hour are obtained. This corresponds to a methanol conversion of 98.7%, a selectivity for $C_2$–$C_4$-olefins of 74.2% and a selectivity for $C_2$–$C_4$-hydrocarbons of 92.6%, if the dimethyl ether and unreacted methanol are recycled.

Hydrocarbon selectivities of only 12% are already achieved after the third regeneration, carried out as in Comparison Example 1, that is to say the addition of water causes irreversible damage to the catalyst.

EXAMPLE 300 ml of a commercial chabasite/erionite mixture in the form of extruded particles (the same molecular sieve as in the two preceding comparison examples) are left to stand for 48 hours in a saturated solution of disodium ethylenediaminetetraacetate of pH 4.45 at room temperature (25° C.) and are then washed, and the sodium is replaced by manganese as in the preceding examples. Under the conditions of Comparison Example 2, and when 57.5 g of methanol and 57.5 g of water and fed in per hour, 7.3 g of unreacted methanol, 73.8 g of water, 5.8 g of dimethyl ether and 64 l of a hydrocarbon mixture consisting of 42.2% by weight of ethylene, 37.6% by weight of propylene, 5.0% by weight of butenes, 7.0% by weight of methane, 1.6% by weight of ethane, 4.9% by weight of propane, 1.2% by weight of butane and 0.5% by weight of other compounds are obtained in the reaction product. This corresponds to a conversion of 87.3%, a selectivity for $C_2$–$C_4$-olefins of 84.8% and a selectivity for $C_2$–$C_4$-hydrocarbons of 92.5%, if unreacted methanol and the dimethyl ether formed are recycled.

After 38 regeneration cycles carried out as in Comparison Example 1, no decrease in the efficiency can be detected and the efficiencies of the fresh catalyst are achieved.

What is claimed is:

1. Process for the manufacture of $C_2$–$C_4$-olefins from methanol and/or dimethyl ether in the presence of water, on an aluminum silicate catalyst containing manganese, which comprises washing the catalyst with a solution of ethylenediaminetetraacetic acid or tartaric acid with a pH of 3 to 7.

2. Process as claimed in claim 1, wherein the solution has a pH of 4–5.

3. Process as claimed in claim 1, wherein the washing is carried out before the application of the manganese to the aluminum silicate.

4. Process as claimed in claim 1, wherein the washing is carried out with a solution of ethylenediaminetetraacetic acid.

5. Process as claimed in claim 1, wherein the pH is established with alkali metal hydroxide.

6. Process as claimed in claim 1, wherein the pH is established with sodium hydroxide or potassium hydroxide.

* * * * *